United States Patent
Sun et al.

(10) Patent No.: US 8,126,239 B2
(45) Date of Patent: Feb. 28, 2012

(54) REGISTERING 2D AND 3D DATA USING 3D ULTRASOUND DATA

(75) Inventors: Yiyong Sun, Lawrenceville, NJ (US);
Rui Liao, Plainsboro, NJ (US);
Chenyang Xu, Allentown, NJ (US);
Frank Sauer, Princeton, NJ (US)

(73) Assignee: Siemens Aktiengesellschaft, München (DE)

( * ) Notice: Subject to any disclaimer, the term of this patent is extended or adjusted under 35 U.S.C. 154(b) by 1167 days.

(21) Appl. No.: 11/874,266

(22) Filed: Oct. 18, 2007

(65) Prior Publication Data

US 2008/0095421 A1    Apr. 24, 2008

Related U.S. Application Data

(60) Provisional application No. 60/853,387, filed on Oct. 20, 2006.

(51) Int. Cl.
*G06K 9/00* (2006.01)
(52) U.S. Cl. ........................................ 382/131; 600/407
(58) Field of Classification Search .................. 382/154, 382/294, 131; 600/407
See application file for complete search history.

(56) References Cited

U.S. PATENT DOCUMENTS

| | | | |
|---|---|---|---|
| 6,711,433 B1 * | 3/2004 | Geiger et al. ................. | 600/431 |
| 6,837,892 B2 * | 1/2005 | Shoham ........................ | 606/130 |
| 2002/0122576 A1 * | 9/2002 | Weese et al. .................. | 382/131 |
| 2003/0220555 A1 * | 11/2003 | Heigl et al. ................... | 600/407 |
| 2005/0245810 A1 * | 11/2005 | Khamene et al. ............. | 600/410 |
| 2006/0078195 A1 * | 4/2006 | Vaillant et al. ................ | 382/154 |
| 2006/0161572 A1 | 7/2006 | Vogt et al. | |
| 2006/0262970 A1 * | 11/2006 | Boese et al. .................. | 382/131 |
| 2007/0047840 A1 * | 3/2007 | Xu et al. ....................... | 382/294 |

OTHER PUBLICATIONS

Rui Lao, et al., "Learning-Based 2D/3D Rigid Registration Using Jensen-Shannon Divergence for Image-Guided Surgery," MIAR, 2006.

* cited by examiner

*Primary Examiner* — Hadi Akhavannik
(74) *Attorney, Agent, or Firm* — Donald B. Paschburg

(57) ABSTRACT

A fluoroscopy image is registered with data representing a volume, identifying a catheter position relative to a volume represented by preoperative volume data. The catheter position relative to a patient volume represented by data acquired without scanning the catheter is displayed. For example, a 2D fluoroscopy image is registered with respect to coordinates of a 3D preoperative CT or MRI volume by registering the fluoroscopy image and the preoperative volume to 3D ultrasound coordinates.

20 Claims, 2 Drawing Sheets

REGISTERING 2D AND 3D DATA USING 3D ULTRASOUND DATA

RELATED APPLICATIONS

The present patent document claims the benefit of the filing date under 35 U.S.C. §119(e) of Provisional U.S. Patent Application Ser. No. 60/853,387, filed Oct. 20, 2007, which is hereby incorporated by reference.

BACKGROUND

The present embodiments relate to registering data representing a patient region. For example, a two-dimensional (2D) fluoroscopic image is registered with preoperative Computed Tomography (CT) or Magnetic Resonance Imaging (MRI) data.

2D X-ray fluoroscopy is routinely used for vascular interventions and for cardiac catheterization. Fluoroscopy is used for real-time monitoring of the procedure and catheter location visualization. However, 2D fluoroscopic images lack detailed anatomical information due to the incapability of X-ray in distinguishing among soft tissues.

In order to augment the doctor's visualization of the body anatomy, for example, in the arterial fibrillation procedures, Intracardiac Echo (ICE) is used as an intra-operative modality to provide real-time cross-sectional ultrasound images. The drawback of ultrasound images compared to the high-quality preoperative volumetric data, such as Computed Tomography (CT) and Magnetic Resonance Imaging (MRI), is that the field of view is limited to local regions and the image quality is inferior with much lower spatial resolution. It is preferred to have CT and/or MRI data to provide high-quality global-view visualization of the body anatomy.

The high-resolution preoperative CT and/or MRI data may be fused with the intra-operative 2D fluoroscopy through 2D3D registration techniques. 2D3D registration techniques are generally intensity-based, centerline-based, and landmark-based, all of which typically require that the vessels of interest in fluoroscopy be opacified by injecting contrast agent into the patient. Without the contrast agent to highlight the vessels, intensity and centerline-based 2D3D registration in a robust manner is difficult. For landmark-based registration, accurate manual selection of 3D points represented by the volumetric data is not easy, and it is not always possible to identity the landmarks in the 2D fluoroscopy image without highlighting the region of interest via contrast agent. The clear structures in the fluoroscopy images, such as catheters and other devices, may not be present in the preoperative 3D volumes. Contrast agent administration may be undesired for patients' safety.

BRIEF SUMMARY

By way of introduction, the preferred embodiments described below include methods, systems, instructions, and computer readable media for registering a fluoroscopy image with data representing a volume, identifying a catheter position relative to a volume represented by preoperative volume data, and/or displaying a catheter position relative to a patient volume represented by data acquired without scanning the catheter. In one embodiment, a 2D fluoroscopy image is registered with respect to coordinates of a 3D preoperative CT or MRI volume by registering the fluoroscopy image and the preoperative volume to 3D ultrasound coordinates.

In a first aspect, a method is provided for registering a fluoroscopy image with data representing a volume. The fluoroscopy image is registered with ultrasound data. The ultrasound data is registered with the data representing the volume. The fluoroscopy image is registered with the data representing the volume as a function of the registrations of the fluoroscopy image with the ultrasound data and the ultrasound data with the data representing the volume.

In a second aspect, a computer readable storage medium has stored therein data representing instructions executable by a programmed processor for identifying a catheter position relative to a volume represented by preoperative volume data. The storage medium includes instructions for spatially aligning a two-dimensional fluoroscopy image within a volume, the aligning being performed with ultrasound data representing the volume, spatially aligning the ultrasound data representing the volume with the preoperative volume data representing the volume, and displaying a position of the two-dimensional fluoroscopy image relative to the preoperative volume data, the position being a function of the spatial alignments of the two-dimensional fluoroscopy image within a volume and the ultrasound data representing the volume with the preoperative volume data representing the volume.

In a third aspect, a system is provided for displaying a catheter position relative to a patient volume represented by data acquired without scanning the catheter. A memory is operable to store the data representing the patient volume. A x-ray fluoroscopy imaging system is operable to generate a projection image of a region including the catheter. An ultrasound imaging system with a transducer is operable to generate ultrasound data representing a scanned volume. The scanned volume at least intersecting a portion of the patient volume. A processor is operable to determine the catheter position relative to the patient volume as a function of the ultrasound data representing the scanned volume. A display is operable to display the catheter position relative to the patient volume.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS 3D tracked ultrasound images bridge registration between the preoperative CT and/or MRI data and intra-operative fluoroscopy. Administration of additional contrast agent may be avoided by using the ultrasound data. For example, preoperative CT and/or MRI coordinates are registered to the ultrasound coordinates via a 3D3D registration based on image or data similarities. This registration may be more robust and accurate than direct 2D3D registration of fluoroscopy data with the preoperative data. The ultrasound imaging system can provide real-time 3D location of the catheter tip. Due to clear visibility in fluoroscopy, the catheter tip may be readily located in fluoroscopy images via an automatic catheter tip localization algorithm. The ultrasound coordinates are registered to the fluoroscopy coordinates by aligning the catheter tip locations. The preoperative volume is registered to the 2D fluoroscopy by a concatenation of the above two registrations.

By utilizing the ultrasound images, which are commonly used by radiologists in interventional procedures, the difficult task of 2D3D registration is decoupled into two more-doable parts. The registration between the ultrasound data and the fluoroscopy data may be performed once, even before starting the interventional procedures, to speed up the workflow. In addition, the catheter can be conveniently moved over a large space without necessarily being inside the patient's body to achieve an accurate, robust, and non-invasive registration. If the patient moves during the intervention, re-registration is performed efficiently by an updated 3D3D registration between the CT and/or MRI volume and the real-time ultrasound images.

The registration may be performed for treatment of any particular organ. Both fluoroscopy and ultrasound images are relatively inexpensive imaging modalities routinely used in interventional procedures. User interaction and online or real-time operation may be provided with reduced time requirements. Additional contrast agent administration may be avoided, but may also be provided.

Figure 1:
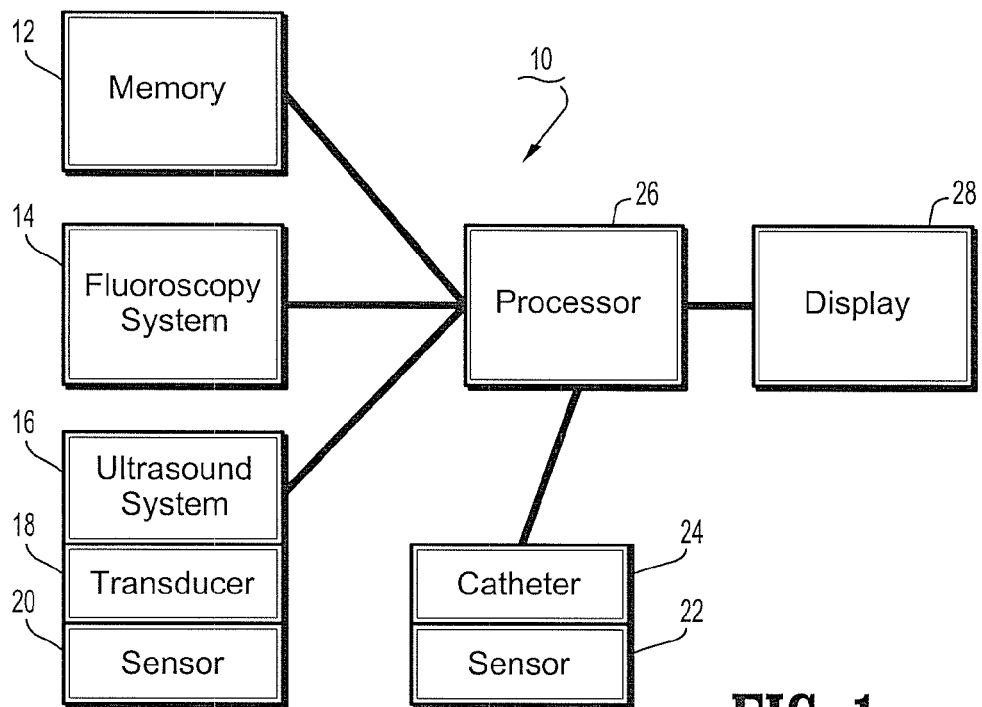
FIG. 1 is a block diagram of one embodiment of a system for displaying a catheter position relative to a patient volume represented by data acquired without scanning the catheter.

FIG. 1 shows a system 10 for displaying a catheter position relative to a patient volume represented by data acquired without scanning the catheter. The system 10 includes a memory 12, a fluoroscopy system 14, an ultrasound system 16, a catheter 24, a transducer 18, one or more sensors 20, 22, a processor 26, and a display 28. Additional, different, or fewer components may be provided. For example, a network or network connection is provided, such as for networking with a medical imaging network or data archival system. As another example, a preoperative imaging system, such as a computed tomography or magnetic resonance imaging system, is provided with or as an alternative to the memory 12. In another example, a user interface is provided.

The processor 26 and display 28 are part of a medical imaging system, such as the diagnostic or therapy ultrasound system 16, fluoroscopy system 14, x-ray, computed tomography, magnetic resonance, positron emission, or other system. Alternatively, the processor 26 and display 28 are part of an archival and/or image processing system, such as associated with a medical records database workstation or server. In other embodiments, the processor 26 and display 28 are a personal computer, such as desktop or laptop, a workstation, a server, a network, or combinations thereof.

The display 28 is a monitor, LCD, projector, plasma display, CRT, printer, or other now known or later developed devise for outputting visual information. The display 28 receives images, graphics, or other information from the processor 26, memory 12, fluoroscopy system 14, or ultrasound system 16.

One or more images representing a catheter position relative to a patient volume are displayed. For example, an image rendered from a three-dimensional data set includes fluoroscopic information showing the location of a catheter within the volume. Preoperative data with higher resolution and real-time fluoroscopic data showing the catheter 24 may be combined prior to rendering or after rendering to generate an image on the display 28. Other images may be displayed, such as a rendering from three-dimensional ultrasound data set or a two-dimensional ultrasound scan. The position of the catheter may be indicated by the ultrasound image or data rendered with preoperative data. The fluoroscopic image may be displayed separately. Any of the types of data may be combined to form an image or displayed separately at a substantially same time. For example, preoperative and fluoroscopic images are displayed separately with or without a separate ultrasound image. As another example, preoperative and fluoroscopic images are displayed separately with an image formed from a combination of the preoperative and fluoroscopic images or data.

The memory 12 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 12 is part of an imaging system, part of a computer associated with the processor 26, part of a database, part of another system, or a standalone device.

The memory 12 stores one or more datasets representing a three-dimensional patient volume. The patient volume is a region of the patient, such as a region within the chest, abdomen, leg, head, arm, or combinations thereof. The patient volume is a region scanned by a medical imaging modality.

Any type of data may be used, such as medical image data (e.g., ultrasound, x-ray, computed tomography, magnetic resonance, or positron emission). In one embodiment, the data representing the patient volume is computed tomography data, magnetic resonance data, or combinations thereof. The data represents the patient prior to or during treatment. For example, CT or MRI data is acquired prior to intervention, such as just prior to (same day) or during a previous appointment on a different day. The data may not include return or response of a catheter. The data represents tissue, preferably in a high resolution.

The data is interpolated or converted to an evenly spaced three-dimensional grid or is in a scan format. Each datum is associated with a different volume location (voxel) in the patient volume. Each volume location is the same size and shape within the dataset. Volume locations with different sizes, shapes, or numbers along a dimension may be included in a same dataset. The data coordinate system represents the position of the scanning device relative to the patient.

The x-ray fluoroscopy system 14 is any now known or later developed fluoroscopy system. For example, the fluoroscopy system 14 includes an x-ray source and an x-ray detector on a C-arm or other robotic mechanism for positioning relative to the patient. A fixed or moveable table or patient support may alternatively or additionally be provided. The fluoroscopic system 14 includes position sensors for determining changes in position of the x-ray source and/or detector.

For fluoroscopic imaging, a contrast agent (e.g., iodine) may be injected into a patient. The contrast agent provides a detectable response to x-rays. By flowing through the circulatory system, the contrast agent may provide detectable response highlighting the circulatory system, such as the vessels, veins, and/or heart. Alternatively, no contrast agent is injected for fluoroscopic imaging. By transmitting x-rays through the patient to the detector, a projection image is provided. Any tissue, bone, catheter, and contrast agent along the path of travel of the x-ray beam interact with the x-rays, causing a detectable difference in intensity at the detector. Since each pixel or location of the detector represents an accumulation of responses along the path of travel, the fluoroscopic image is a projection image of the region.

A fluoroscopic image may be generated with or without response from the catheter 24. For example, the catheter 24 is positioned in the x-ray beam adjacent to but outside the patient. Such positioning may be used for an initial registration with an ultrasound system. A fluoroscopic image is generated with response from the catheter. During intervention, the catheter may be positioned within the patient. One or more fluoroscopic images are generated in real-time or during the interventional procedure.

The x-ray beam of the fluoroscopy system 14 may pass through or intersect the patient volume. For example, the catheter 24 is to be used for ablation of heart wall tissue. The patient volume includes at least a portion of the heart. The x-ray beam is positioned to also project through the heart.

The ultrasound system 16 is any now known or later developed ultrasound imaging system. For example, the ultrasound system 16 includes the transducer 18 for converting between acoustic and electrical energies. Transmit and receive beamformers relatively delay and apodize signals for different elements of the transducer 18. B-mode, Doppler, or other detection is performed on the beamformed signals. A scan converter, memory, three-dimensional imaging processor, and/or other components may be provided.

The transducer 18 is a one-, two-, or multi-dimensional array of piezoelectric or capacitive membrane elements. In one embodiment, the transducer 18 is a handheld or machine held transducer for positioning against and outside of the patient. In another embodiment, the transducer 18 is part of a probe for use within the patient, such as a transesophageal probe. For example, the transducer 18 is a one-dimensional array of elements within or on the catheter 24 used for intervention or a different catheter.

The ultrasound data is output in a polar coordinate or scan converted Cartesian coordinate format. Acoustic energy is used to scan a plane and/or volume. For example, a volume is scanned by sequentially scanning a plurality of adjacent planes. Any format or scan technique may be used. The scanned volume may intersect or include all of the patient volume. For example, the heart is scanned with ultrasound.

The catheter 24 is any now known or later developed catheter for intervention or other use within a patient. The catheter 24 is sized and shaped for use in the circulatory system, such as having a diameter of 10 French or less, but a length of a foot or more. The catheter 24 is adapted for insertion within the patient, such as through a vessel or vein for extending into a heart chamber. The catheter 24 may include guide wires or be inserted through another previously positioned housing or catheter. The catheter 24 includes an electrode, scalpel, balloon, stent, or other device for treatment of the heart or circulatory system.

One or more sensors 20, 22 provide position information. For example, the sensor 20 is operable to determine a location of the transducer 18. The sensor 20 is a magnetic position sensor, such as three orthogonal coils and a magnetic field generator. The coils or field transmission antenna are positioned in the transducer 18. The other of the field transmission antenna or the coils are positioned outside the patient. The position of the transducer 18 relative to the location outside of the patient is sensed. Other position sensors may be used, such as acoustic sensors, or radio frequency sensors. Data from the scan may be used to determine position, such as correlating the ultrasound data with a model.

One position sensor 22 is operable to determine a location of the catheter 24, such as a tip of the catheter 24. For example, one of the types of sensors discussed above for sensor 20 is used. In one embodiment, a magnetic sensor, such as from Biosense Webster, Inc., is integrated with an imaging catheter, such as the Siemens AcuNav catheter. The sensor 22 allows locating the tip or other portion of the catheter 24. When the catheter 24 includes the transducer 18, the same sensor 20, 22 may be used for transducer and catheter location.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position and/or generating images. The processor 26 is a single device or multiple devices operating in serial, parallel, or separately. The processor 26 may be a main processor of a computer, such as a laptop or desktop computer, or may be a processor for handling some tasks in a larger system, such as in an imaging system.

The processor 26 determines a catheter position relative to the patient volume. The position may be determined for establishing coordinate relationships prior to insertion within a patient, such as for establishing the relationship between the fluoroscopy system 14 and the ultrasound system 16. The position may be determined during the intervention or use of the catheter 24.

The position of the catheter relative to the patient volume is determined as a function of the ultrasound data representing the scanned volume. The spatial relationship of the fluoroscopic data is determined relative to the ultrasound data. The region of the fluoroscopic projection is registered with the scanned volume. The spatial relationship of the preoperative or other three-dimensional imaging data is determined relative to the ultrasound data. The ultrasound-scanned volume is registered with the patient volume of the preoperative or other imaging data. The spatial relationships or registrations are used to determine the catheter position as represented in the fluoroscopic region relative to the tissue represented in the preoperative or other imaging data. The processor 26 uses the ultrasound scan and/or ultrasound transducer position data as an intermediary.

To register the ultrasound data with the fluoroscopy data, the coordinate relationship between the x-ray fluoroscopy imaging system and the ultrasound system is determined. The sensed location of the catheter 24 and/or the transducer 18 are used to register. The sensor 22 and/or sensor 20 provide a location of the catheter 24. The catheter 24 may be within or outside of the patient for the registration. One or more locations may be used, such as sensing a sequence of locations.

A fluoroscopic image is generated with the catheter 24 within the region of projection. One or more images may be generated, such as generating an image for each location of the catheter 24 that is sensed and recorded. The processor 26 processes the image to identify the catheter location within the image. The user may assist the processing by indicating the catheter and/or orientation within the image. For fully automated operation, the processor 26 performs a series of pattern matches. Different reference images or catheter patterns are matched to the image. The reference or pattern with the best match indicates a catheter position relative to the fluoroscopy system 14. Other image processing may be used.

The catheter tip or other portion of the catheter position relative to the fluoroscopic image is aligned with the tip or other portion relative to the ultrasound data using from the sensor 20, 22. The relative position and/or orientation of the fluoroscopic system 14 and the ultrasound transducer 18 is determined. This offset in position and/or orientation indicates the coordinate relationship between the two systems 14, 16.

Accuracy may be increased by identifying the catheter in more than one fluoroscopic image and at a respective more than one location. The offset for each pair is used to determine an overall offset or relative coordinate space, such as by averaging.

As the fluoroscopic system 14 moves for imaging, the position and orientation change is determined. The change information may be used with the determined offset to track the relative positions without further registration. Similarly, changes in the transducer position or orientation may be tracked with the sensor 20, allowing determination of relative coordinates without further registration. Further registration may be used, such as a check or for re-calibrating.

The processor 26 registers the ultrasound data with the data representing the patient volume. Similarities between the ultrasound data and the data representing the patient volume are identified. Image processing may identify features. The user may identify features. Identifying three or more features or one or more features with a corresponding orientation represented by both data sets indicates relative positioning of the patient volume and the scanned volume.

Alternatively, similarity is determined using a correlation, such as a minimum sum of absolute differences, cross correlation, autocorrelation, or other correlation. For example, a two or three-dimensional set of data is translated and/or rotated into various positions relative to another set of data. The relative position with the minimum sum or highest correlation indicates a match, alignment, or registration location. The set of data may be sub-set, such as a region of interest or a decimated set, or may be a full set. The set to be matched may be a sub-set or full set, such as correlating a decimated region of interest sub-set of ultrasound data with a full set of preoperative data.

The relative positioning indicates a translation and/or rotation of one set of data relative to another set of data. The coordinates of the different volumes may be aligned or transformed such that spatial locations in each set representing a same tissue have a same or determinable location.

For a catheter procedure, the fluoroscopy system 14 is registered relative to the ultrasound system 16. A spatial alignment is determined for the fluoroscopy projection region relative to the ultrasound scanned region or ultrasound coordinate space. For example, the ultrasound coordinate space corresponds to the position sensor 22 on an ultrasound imaging catheter (e.g., a catheter 24 with the transducer 18). The registration is determined prior to or during the catheter procedure. During the procedure, an ultrasound scan and fluoroscopy imaging are performed. The coordinate systems for both are aligned, allowing identification of data from the same spatial locations. The ultrasound data representing the scanned volume is matched to preoperative or other data. For example, 3D ultrasound data is correlated with 3D CT or MRI data. The matching registers the coordinates, allowing identification of data from the same spatial locations. The two registrations with the ultrasound coordinate space allow registration of the fluoroscopic data with the preoperative or other data. The registration is provided by geometric relationship.

Spatially aligned data may be combined, such as by summing, averaging, alpha blending, maximum selection, minimum selection or other process. For example, preoperative data is combined by replacing preoperative values associated with a catheter identified from a fluoroscopic image. The combined data set is rendered as a three-dimensional representation. The catheter represented in the fluoroscopic data is provided in the rendering from the tissue responsive preoperative data. The catheter may be highlighted, such as by filtering, increasing voxel values, saturation, or other technique in the combination. In an alternative embodiment, a three-dimensional representation is rendered from the preoperative or other tissue responsive data. The fluoroscopic data is rendered separately and overlaid or shown adjacent to the tissue data rendering. A 2D region or volume may be replaced with ultrasound data to provide real-time feedback about catheter position and tissue relative to the preoperative rendering.

The memory 12 or other memory is a computer readable storage medium storing data representing instructions executable by the programmed processor 26 for identifying a catheter position relative to a volume represented by preoperative volume data. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Figure 2:
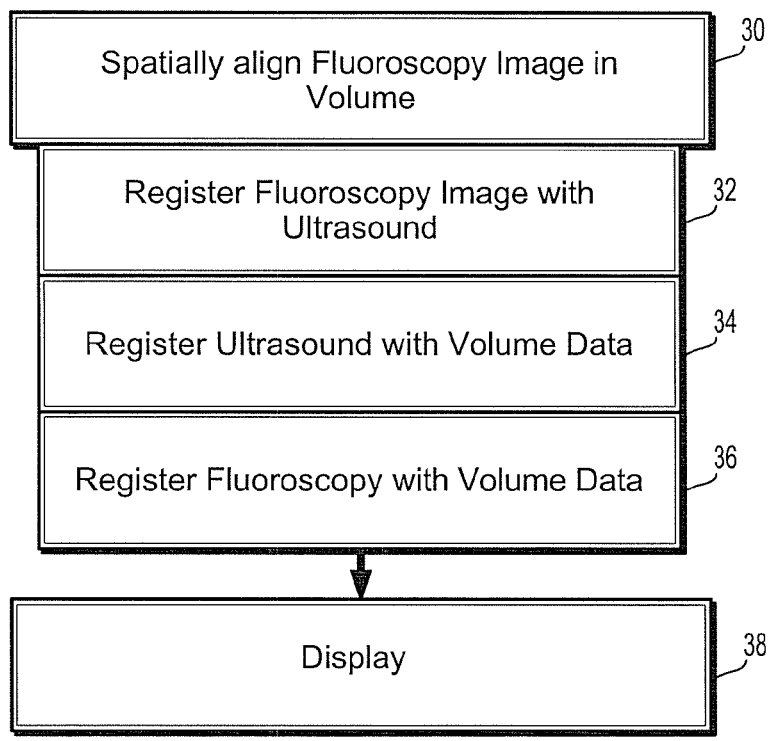
FIG. 2 is a flow chart diagram of one embodiment of a method for registering a fluoroscopy image with data representing a volume.

FIG. 2 shows a method for registering a fluoroscopy image with data representing a volume. The method is implemented by the system 10 of FIG. 1 or another system. The acts are performed in the order shown or other orders. Additional, different, or fewer acts may be provided. For example, the display act 38 is not provided, but instead the registered data is used to control scanning or imaging. As another example, user input is provided for selecting display, controlling combination, controlling registration, or other purposes.

In act 30, a two-dimensional fluoroscopy image is spatially aligned within a volume. The alignment is relative to an ultrasound coordinate system. The ultrasound data is aligned with the two-dimensional fluoroscopy image, such as by aligning the fluoroscopic and ultrasound coordinate spaces. Data representing the volume (e.g., preoperative data) is also aligned with the ultrasound data. The data representing the volume is aligned with the fluoroscopy images based on the ultrasound data representing a scanned volume. Acts 32, 34, and 36 represent the method for spatially aligning fluoroscopy images with a volume, such as a volume represented by preoperative data (e.g., CT or MRI). Additional, different, or fewer acts may be performed.

In act 32, one or more fluoroscopy images are registered with ultrasound data. The fluoroscopy image represents a two-dimensional region of a volume. The ultrasound data represents the volume. The image and ultrasound data are registered by data matching, sensor measurements, or combinations thereof. The coordinate systems are aligned or other process performed to identify voxels or spatial locations representing the same region given a viewing angle. In one embodiment, the registration is of a two-dimensional fluoroscopic image with a three-dimensional volume in ultrasound or sensor coordinate space (e.g., 2D3D registration).

A position and orientation of the ultrasound data relative to the volume is detected, such as detecting with a sensor associated with the transducer. The accurate 3D location of the catheter tip can be provided by the tracked ultrasound imaging system.

The position and orientation of the fluoroscopic image relative to the catheter is detected. The catheter in the fluoroscopic image is identified. The corresponding 2D location can be detected automatically in fluoroscopy because of the high attenuation property of the catheter for X-ray. The catheter is identified in the fluoroscopy image by pattern matching. For example, a plurality of reference images or models of the catheter at different orientations and positions are compared to the fluoroscopic image. The catheter may be identified initially in the image to reduce the number of matches. Alternatively, each different reference or model is rotated and/or translated to identify a best or sufficient match. The best matches for the respective references or models are compared to determine a highest correlation or match. The position and orientation of the reference or model associated with the highest match provides the position and orientation of the catheter in the fluoroscopic image. Interpolation, extrapolation, numerical optimization or other process may be used to provide higher resolution matching than available references or models. Other processes to determine the position and orientation of the catheter in the fluoroscopic image may be used.

A position and orientation of a feature, such as the catheter, in the fluoroscopy image is determined. The two catheter positions and orientations are aligned spatially (e.g., the two-dimensional fluoroscopy image and a coordinate system of the ultrasound data are aligned as a function of the catheter position). The catheter has a known position relative to coordinates of the ultrasound data. For example, a sensor provides an indication of the transducer position and corresponding ultrasound scan volume. The position and orientation of the fluoroscopic image is aligned with the ultrasound data as a function of the catheter position and orientation information. The catheter has a detectable position relative to the volume based on the registration.

In alternative embodiments, the ultrasound data is acquired with the catheter in the scanned volume. Image processing may be used to align the catheter in the ultrasound data with the catheter in the fluoroscopy data without use of the position sensors.

Time-consuming and error-prone manual landmark picking may be avoided due to automatic image processing to determine catheter position. Alternatively, the user assists in catheter identification and/or registration. Other landmarks instead of or in addition to the catheter may be used for registration of the fluoroscopic system to the ultrasound system. A plurality of landmarks can be obtained offline for more accurate and robust registration between the ultrasound images and the fluoroscopy. Using the catheter may allow for less overlap of the fluoroscopic region with the ultrasound scanned volume.

The spatial alignment between the two-dimensional fluoroscopy image and the ultrasound data is performed prior to an ablation or other catheter procedure. For example, the catheter is positioned at one or more locations within the x-ray beam of the fluoroscopy system but outside of the patient. The position sensor of the catheter determines the catheter position. The catheter is imaged by the fluoroscopy system, allowing registration of the sensed catheter position and the fluoroscopy system. Later ultrasound imaging is performed relative to the position sensor coordinate system, such as using the catheter with the position sensor for ultrasound imaging or by using a different transducer sensor operating in the same coordinate or sensing system as the catheter sensor.

Online operation or registration while the catheter is being used in the patient may be minimized. Before the intervention, offline registration between the ultrasound images and the fluoroscopy can be obtained by acquiring a sufficient number of catheter tip locations over a large space by moving the catheter tip freely. Multiple measurements of the catheter position may provide registration that is more accurate. This registration may be performed only once, but may be performed at other times (e.g., during the catheter procedure).

In act 34, the ultrasound data is registered with the data representing the volume (e.g., preoperative data). The ultrasound data representing the volume is spatially aligned with the preoperative volume data representing the volume.

The preoperative data represents a volume of the patient. The data is acquired prior to insertion of the catheter. For example, a CT or MRI scan is performed of the patient earlier in the day or on a previous day. The scan is of a three-dimensional region of the patient, providing a set of data representing tissue in the volume. The data does not include response from the catheter. In alternative embodiments, other imaging modalities are used, and/or a two-dimensional region is scanned without scanning a three-dimensional region. The scanning may be performed during the catheter procedure, resulting in the data including response from the catheter.

The ultrasound data is acquired. The transducer is maintained in one position or moved to scan a volume. Electronic, mechanical, automatic, and/or manual positioning of the scan lines is used to acquire ultrasound data representing a three-dimensional volume. The scanned volume is the same as, or at least overlaps, the volume of the preoperative scan (e.g., CT or MRI volume). In alternative embodiments, a two-dimensional scan is performed without scanning in three-dimensions.

The ultrasound data is acquired during or prior to the catheter procedure. By acquiring the data during the procedure, shifts in the patients position relative to the ultrasound coordinates and registered fluoroscopy system may be tracked. The tissue represented in the ultrasound data and the preoperative data is registered to account for the patient movement.

Registering is performed along two or three-dimensions. Inter-modality 3D-3D registration may provide registration more accurate than 2D-3D or 2D-2D. The registration accounts for rotation along any number of the dimensions. Any combination of translation and rotation degrees of freedom may be used, such as 6 degrees (3 axes of rotation and 3 axes of translation).

The coordinates of the ultrasound and other modality are registered, such as by using position sensors. In other embodiments, the data from the ultrasound and other modality are registered using any now known or later developed data registration. For example, manual alignment of images rendered from the data or automatic image- or data-based registration may be used.

In one embodiment, the data sets prior to rendering are correlated. For example, the ultrasound data is correlated with the data representing the volume. Different translations and rotations between the sets of data are searched and a corresponding similarity value is calculated. The translation and rotation combination with the highest or sufficient correlation indicates the spatial alignment. Any search pattern may be used, such as numerical optimization, course-to-fine searching, subset based searching, or use of decimated data.

The correlation may be based on all of the data in the sets or as a function of at least one feature represented in the ultrasound data and the data representing the volume. For example, the user or a processor identifies features in each data set. The features may be tissue boundaries, tissue regions, bone region, fluid region, air region, combinations thereof, or other feature. The data representing the features with or without surrounding data is used for the correlation. The features may be identified in one set (e.g., ultrasound) for matching with all of the data in another set, or features of one set may be matched to features of another set.

The data may be used for correlation without alteration. In other embodiments, one or both sets of data are filtered or processes to provide more likely matching. For example, higher resolution CT or MRI data is low pass filtered, decimated, or image processed to be more similar to ultrasound data.

One example embodiment for registering CT data set and an ultrasound data set uses CT data acquired with an Angiographic C-arm system (AXIOM Artis, Siemens Medical Solutions). To image the left atrium of a patient, images are acquired during 4 consecutive rotational 190° C.-arm runs to get enough images to reconstruct a 3D image of one cardiac phase. Each run has multiple (e.g., 247) frames at any speed (e.g., 60 frames per second). The radiation dose is 1.2 µGy per frame. For visualization, the left atrium and other heart structures are segmented using dedicated software. Other preoperative scanning (e.g., speeds, number of rotations, amount of rotation, number of frames, radiation dose, or other modality) may be used.

For ultrasound data, images are acquired from the catheter (AcuNav, Siemens Medical Solutions). A magnetic tracking system (Microbird, Ascension) tracks the position of the catheter tip. This position sensor is integrated in the same tubing or catheter housing with the ultrasound transducer. The sensor transmitter is installed under the table of the C-arm system, such that the catheter above the table is within the operating range and can be tracked during an intervention. During ultrasound imaging, the ECG signal of the patient is recorded, and the position sensor at the catheter tip and the other position sensor at the patient's chest (for respiratory motion correction) are tracked simultaneously.

The coordinate system of the tracking device or sensor may be denoted as W, and the coordinate system of the sensor when acquiring the ith ultrasound frame is denoted as $S_i$. The tracking sensor provides transformation matrix $T_{Si}$ of $S_i$ relative to W. The position of an ultrasound voxel $S_i$ is determined by a scaling matrix $T_S$ and a transformation $T_C$ provided by an offline calibration. An ultrasound voxel $\rho_{US}$ is mapped to a point in the CT coordinate system by $\rho_{CT} = T_R \cdot T_{Si} \cdot T_C \cdot T_S \cdot \rho_{US}$, where $T_R$ is the registration matrix to be estimated.

Heart motion and respiratory motion are factors that influence the accuracy of registration. To eliminate or reduce the respiratory motion from the data to be registered, the displacement in the Z-axis (e.g., up and down relative to the floor or patient) of the second sensor placed on the patient's chest is analyzed. Data acquired without significant chest movement is selected and used. To detect the respiratory rest phases, the position variance of the sensor in the Z-axis during the previous 50 or other number of acquired frames is computed. If the variance is below a threshold, the frames are used. The threshold can be adjusted during the ultrasound acquisition.

The data acquired at a set time interval from the previous R-wave in the ECG signal is selected (e.g., cardiac gating). Triggering of the acquisition may alternatively be used. About 3 cardiac gated frames of data are selected for each respiration in one example. The doctor puts the catheter in the right atrium and sweeps the catheter across the heart chambers. When a qualified frame is selected, the system notifies the doctor to proceed to another orientation or position.

The registration process computes a rigid transformation from the coordinate system of the tracking device to the C-arm CT space. Because the ultrasound images the heart and the CT image contains the whole thorax of the subject, an initial alignment between the systems is performed before applying an automatic search for six registration parameters (i.e., translation and rotation in six degrees of freedom). Since the tracking device is fixed under the table, an initial rotation can be estimated from the axes of the tracking transmitter and the patient orientation of the C-arm CT data. An initial translation can be estimated by asking the user to either select a point in the 3D data corresponding to the tip location, or manually match the ultrasound data and a Multiplanar Reconstruction (MPR) of the 3D CT data. Automated initial registration may be used. The estimation may be accurate or inaccurate. If the segmentation of the C-arm CT data is available, the centroid of the right atrium segmentation can be used to initialize the registration.

The initial registration is followed by an automatic registration. The registration parameters are optimized according to the similarity between the gated ultrasound data and the corresponding CT data. Because the ultrasound response has high intensity at the chamber boundary and low intensity values inside the chamber, the gradient magnitude of the CT data is used for the similarity computation. The gradient at each voxel of the CT volume is computed using a 3D Sobel or other filter before applying the registration. The high gradient magnitude outside the heart chamber can affect the accuracy of registration results because this gradient may not occur in the ultrasound data. The CT intensities may be thresholded to create a mask. The mask is applied to the gradient magnitude image to remove the undesired information. The threshold value can be adjusted interactively from the user interface.

A Normalized Cross-Correlation (NCC) is computed for each translated and/or rotated pairs of the ultrasound and CT gradient magnitude data. The computation may be for the three-dimensional data set or for planar regions based on the initial alignment. The CT gradient data is re-sliced to planes corresponding to the ultrasound data. For planar regions, the sum of all NCC values for the different pairs of planes of ultrasound and CT gradient data may be the similarity measure. The similarity is measured for data located inside a pre-defined shape of the ultrasound data, such as sector or Vector® regions.

The best neighbor method may be used in the optimization. An initial step size is first chosen. In each iteration, all of the parameters are changed in turn with the step size and the value of similarity measure is computed. The change that causes the greatest improvement in the similarity measure is kept. This iteration continues until no change can give a better similarity measure. Then, the step size is reduced and the above process is repeated again. In one embodiment, an initial step size of 5.5 mm or 5.5 degree is used. The step size is reduced by a factor of 2 when needed. The minimum step size is 0.1 mm or 0.1 degree. Other step sizes, amounts of reduction, and/or minimum steps may be provided. A Powell method and/or a gradient decent method may be used.

In act 36, the fluoroscopy image is registered with the data representing the volume. The registration of the fluoroscopy data with the ultrasound data provides one transform, such as a translation and orientation in three-dimensions. The registration of the ultrasound data with the other data (e.g., CT or MRI) provides another transform. The two transforms are combined, such as by matrix multiplication, to register the fluoroscopy image with the data. The coordinate systems of the three modalities are aligned using any geometric transform.

In act 38, a position of the two-dimensional fluoroscopy image relative to the preoperative or other volume data is displayed, such as displaying a wire frame or graphic representing the projection direction relative to a rendering direction for the 3D imaging. In other embodiments, the registered data is combined. In one embodiment, a fluoro projection image is blended with a CT volume rendered image. Alternatively, the spatial alignment is used to overlay rendered or generated images. The relative position in the image or between images is a function of the spatial alignments of the two-dimensional fluoroscopy image within the volume and the ultrasound data representing the volume with the preoperative volume data representing the volume.

Figure 3:
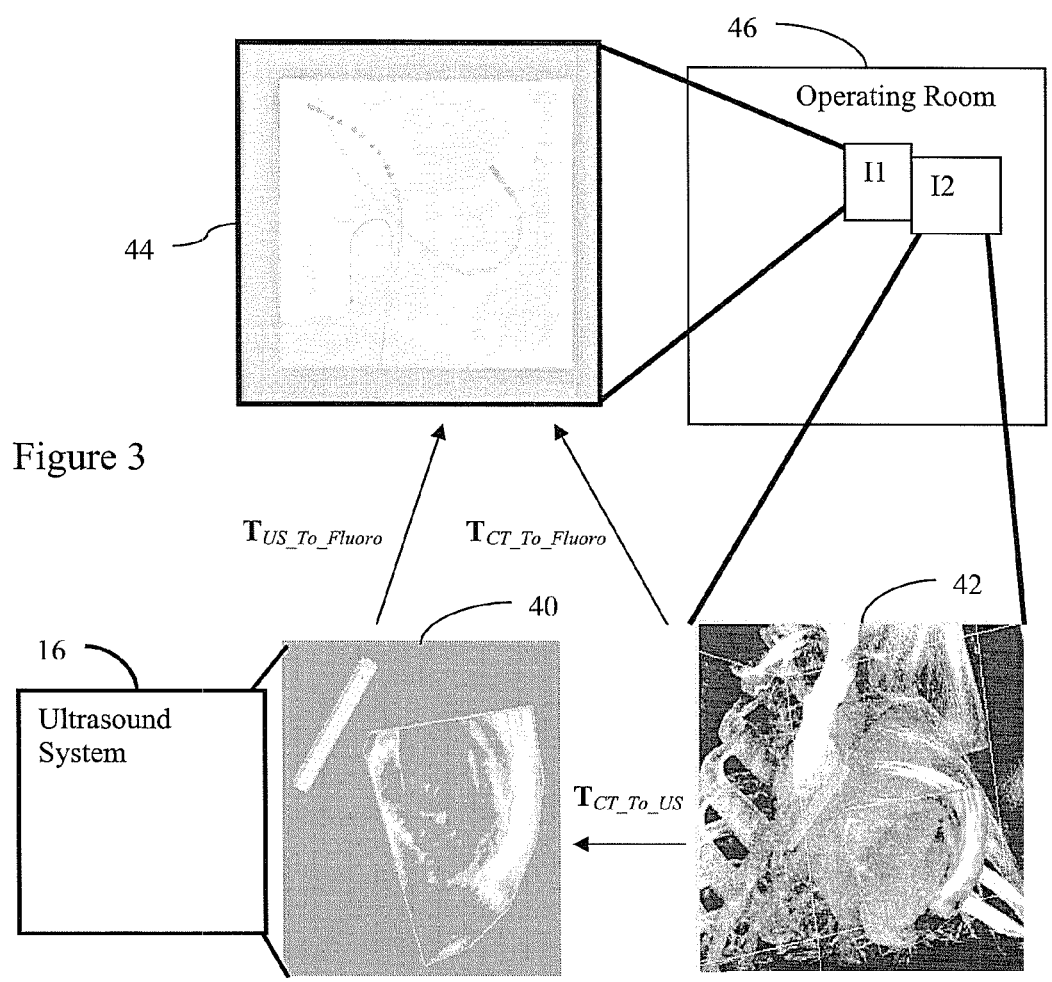
FIG. 3 is a graphical representation of images associated with the registrations of FIGS. 1 and/or 2.

FIG. 3 shows one example. An ultrasound system 16 acquires an ultrasound image 40. The ultrasound image 40 is combined with a three-dimensional rendering 42 from CT data. The transducer position, indicated by a bar, is represented in both the ultrasound image 40 and the CT rendering 42. The transducer position also indicates the catheter position. The fluoroscopy projection image 44 is displayed separately, but may include spatial information associating the fluoroscopy projection image 44 with the CT rendering. For example, the transducer position in the CT rendering 42 indicates the position of the catheter also shown in the fluoroscopy projection image 44. A graphic or other indicator may be provided in the CT rendering 42, such as shown with the ultrasound scan, to indicate the beam direction or other spatial characterization for the fluoroscopy projection image 44. The fluoroscopy projection image 44 may be rendered from a viewing direction corresponding to the view direction of the CT data rendering 42. The spatial transforms are used to indicate spatial relationship and/or to combine data for generating a multiple modality image.

As the catheter changes position, a new fluoroscopy projection image is generated. The spatial relationship may be updated by registering the preoperative data with a ultrasound data from new ultrasound scan. The spatial information or images assist the medical professional in identifying proper positioning of the catheter. One or more images may be provided in an operating room 46 to assist the procedure. The spatial relationship information may be obtained easily by updating the ultrasound scan, and without data responsive to contrast agent within a patient.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for registering a fluoroscopy image with data representing a volume, the method comprising:
   registering the fluoroscopy image with ultrasound data;
   registering the ultrasound data with the data representing the volume; and
   registering the fluoroscopy image with the data representing the volume as a function of the registrations of the fluoroscopy image with the ultrasound data and the ultrasound data with the data representing the volume.

2. The method of claim 1 wherein registering the ultrasound data with the data representing the volume comprises registering the ultrasound data with computed tomography data representing the volume, the fluoroscopy image representing a two-dimensional region of the volume.

3. The method of claim 1 wherein registering the ultrasound data with the data representing the volume comprises registering the ultrasound data with magnetic resonance data representing the volume, the fluoroscopy image representing a two-dimensional region of the volume.

4. The method of claim 1 wherein the ultrasound data comprises a set of data representing the volume, and wherein the data representing the volume comprises non-ultrasound data.

5. The method of claim 1 further comprising detecting a position and orientation of the ultrasound data relative to the volume, and wherein registering the fluoroscopy image with ultrasound data comprises identifying a position and orientation of a feature in the fluoroscopy image.

6. The method of claim 1 wherein registering the ultrasound data with the data representing the volume comprises correlating the ultrasound data with the data representing the volume, the correlating being a function of at least one feature represented in the ultrasound data and the data representing the volume.

7. The method of claim 1 wherein registering the fluoroscopy image with the data representing the volume as a function of the registrations of the fluoroscopy image with the ultrasound data and the ultrasound data with the data representing the volume comprises determining a position and orientation of the fluoroscopy image relative to the data representing the volume as a function of a position and orientation of the fluoroscopy image relative to the ultrasound data and a position and orientation of the ultrasound data relative to the data representing the volume.

8. The method of claim 1 wherein registering the fluoroscopy image with ultrasound data is performed prior to an ablation procedure, wherein registering the ultrasound data with the data representing the volume is performed during the ablation procedure.

9. The method of claim 1 wherein registering the fluoroscopy image with ultrasound data comprises identifying a catheter in the fluoroscopy image, the catheter having a known position relative to coordinates of the ultrasound data.

10. The method of claim 1 wherein the three registering acts are performed free of data responsive to contrast agent within a patient.

11. In a non-transitory computer readable storage medium having stored therein data representing instructions executable by a programmed processor for identifying a catheter position relative to a volume represented by preoperative volume data, the storage medium comprising instructions for:
    spatially aligning a two-dimensional fluoroscopy image within a volume, the aligning being performed with ultrasound data representing the volume;
    spatially aligning the ultrasound data representing the volume with the preoperative volume data representing the volume; and
    displaying a position of the two-dimensional fluoroscopy image relative to the preoperative volume data, the position being a function of the spatial alignments of the two-dimensional fluoroscopy image within a volume and the ultrasound data representing the volume with the preoperative volume data representing the volume.

12. The non-transitory computer readable storage medium of claim 11 wherein spatially aligning the two-dimensional fluoroscopy image comprises:

identifying a catheter position in the two-dimensional fluoroscopy image, the catheter having a detectable position relative to the volume; and aligning the two-dimensional fluoroscopy image and a coordinate system of the ultrasound data as a function of the catheter position.

13. The non-transitory computer readable storage medium of claim 11 wherein spatially aligning the ultrasound data with the preoperative volume data comprises:

identifying similar features represented by the ultrasound data and the preoperative volume data; and aligning the coordinate systems of the ultrasound data and the preoperative volume data as a function of the similar features.

14. The non-transitory computer readable storage medium of claim 11 wherein spatially aligning the two-dimensional fluoroscopy image is performed prior to an ablation procedure.

15. A system for displaying a catheter position relative to a patient volume represented by data acquired without scanning the catheter, the system comprising:

a memory operable to store the data representing the patient volume;

a x-ray fluoroscopy imaging system operable to generate a projection image of a region including the catheter;

an ultrasound imaging system comprising a transducer, the ultrasound imaging system operable to generate ultrasound data representing a scanned volume, the scanned volume at least intersecting a portion of the patient volume;

a processor operable to determine the catheter position relative to the patient volume as a function of the ultrasound data representing the scanned volume; and a display operable to display the catheter position relative to the patient volume.

16. The system of claim 15 further comprising:

a first position sensor operable to determine a first location of the catheter; and a second position sensor or the first position sensor operable to determine a second location of the transducer;

wherein the processor is operable to determine a coordinate relationship between the x-ray fluoroscopy imaging system and the ultrasound system as a function of the first and second locations.

17. The system of claim 16 wherein the first location is outside a patient, the x-ray fluoroscopy system operable generate a first image with the catheter at the first location, and wherein the processor is operable to identify the catheter in the first image and operable to determine the coordinate relationship as a function of the second location and a position of the catheter in the first image.

18. The system of claim 15 wherein the processor is operable to determine similarities between the ultrasound data and the data representing the patient volume and align the patient and scanned volumes as a function of the similarities.

19. The system of claim 15 wherein the data representing the patient volume comprises computed tomography data, magnetic resonance data, or combinations thereof.

20. The system of claim 15 wherein the processor is operable to register the region with the scanned volume, and operable to register the scanned volume with the patient volume, the catheter position relative to the patient volume being a function of the registrations of the region with the scanned volume and the scanned volume with the patient volume.

* * * * *